US011375993B2

(12) United States Patent
Deuel et al.

(10) Patent No.: US 11,375,993 B2
(45) Date of Patent: Jul. 5, 2022

(54) ENDOSCOPIC HANDLE ATTACHMENT FOR USE WITH SUTURE BASED CLOSURE DEVICE

(71) Applicant: BOSTON SCIENTIFIC SCIMED, INC., Maple Grove, MN (US)

(72) Inventors: Christopher R. Deuel, Melrose, MA (US); Shaun Dennis Comee, Fiskdale, MA (US); Evan Hunter Williams, Cambridge, MA (US); Andrew Jones, Roslindale, MA (US); Richard L. Miller, Needham, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 581 days.

(21) Appl. No.: 16/446,201

(22) Filed: Jun. 19, 2019

(65) Prior Publication Data

US 2019/0380701 A1  Dec. 19, 2019

Related U.S. Application Data

(60) Provisional application No. 62/848,853, filed on May 16, 2019, provisional application No. 62/794,075, (Continued)

(51) Int. Cl.
*A61B 17/04* (2006.01)
*A61B 1/00* (2006.01)
(Continued)

(52) U.S. Cl.
CPC ...... *A61B 17/0469* (2013.01); *A61B 1/00066* (2013.01); *A61B 1/00133* (2013.01);
(Continued)

(58) Field of Classification Search
CPC ............ A61B 1/00131; A61B 1/00135; A61B 1/00066; A61B 17/0469
See application file for complete search history.

(56) References Cited

U.S. PATENT DOCUMENTS 5,478,344 A   12/1995 Stone
5,584,861 A   12/1996 Swain et al.
(Continued)

FOREIGN PATENT DOCUMENTS

CA        2682488 A1    10/2008
DE   202005022017 U1    5/2012
(Continued)

OTHER PUBLICATIONS

International Search Report and Written Opinion dated Aug. 20, 2019 for International Application No. PCT/US2019/033748.
(Continued)

*Primary Examiner* — Wade Miles
(74) *Attorney, Agent, or Firm* — Seager, Tufte & Wickhem, LLP

(57) ABSTRACT

An endoscopic handle attachment is adapted to be secured to an endoscope having a working channel and used in combination with a suture device adapted to extend through the working channel. The attachment includes a backbone adapted to conform to an outer surface of the endoscope and that includes one or more attachment features adapted to enable releasable securement to the endoscope. A primary arm extends radially outwardly from the backbone and includes one or attachment points, at least one of the one or more attachment points adapted to releasably secure a proximal handle of the suture device such that a translation handle may be moved relative to the proximal handle without an operator needing to separately hold the proximal handle.

18 Claims, 17 Drawing Sheets

Related U.S. Application Data filed on Jan. 18, 2019, provisional application No. 62/686,923, filed on Jun. 19, 2018.

(51) Int. Cl.
- *A61B 1/018* (2006.01)
- *A61B 10/04* (2006.01)
- *A61B 17/06* (2006.01)
- *A61B 17/00* (2006.01)

(52) U.S. Cl.
CPC .............. *A61B 1/018* (2013.01); *A61B 10/04* (2013.01); *A61B 17/0482* (2013.01); *A61B 1/0008* (2013.01); *A61B 17/06166* (2013.01); *A61B 2017/0034* (2013.01); *A61B 2017/0042* (2013.01); *A61B 2017/00367* (2013.01); *A61B 2017/00424* (2013.01)

(56) References Cited

U.S. PATENT DOCUMENTS

| | | | |
|---|---|---|---|
| 6,086,608 | A | 7/2000 | Ek et al. |
| 6,200,329 | B1 | 3/2001 | Fung et al. |
| 6,402,715 | B2 * | 6/2002 | Manhes .............. A61B 1/00135 604/35 |
| 6,494,888 | B1 | 12/2002 | Laufer et al. |
| 6,506,196 | B1 | 1/2003 | Laufer |
| 6,554,845 | B1 | 4/2003 | Fleenor et al. |
| 6,569,085 | B2 | 5/2003 | Kortenbach et al. |
| 6,626,917 | B1 | 9/2003 | Craig |
| 6,663,639 | B1 | 12/2003 | Laufer et al. |
| 6,719,763 | B2 | 4/2004 | Chung et al. |
| 6,740,030 | B2 | 5/2004 | Martone et al. |
| 6,746,457 | B2 | 6/2004 | Dana et al. |
| 6,755,843 | B2 | 6/2004 | Chung et al. |
| 6,773,441 | B1 | 8/2004 | Laufer et al. |
| 6,808,491 | B2 | 10/2004 | Kortenbach et al. |
| 6,821,285 | B2 | 11/2004 | Laufer et al. |
| 6,835,200 | B2 | 12/2004 | Laufer et al. |
| 6,908,427 | B2 | 6/2005 | Fleener et al. |
| 6,997,931 | B2 | 2/2006 | Sauer et al. |
| 7,056,284 | B2 | 6/2006 | Martone et al. |
| 7,063,710 | B2 | 6/2006 | Takamoto et al. |
| 7,063,715 | B2 | 6/2006 | Onuki et al. |
| 7,094,246 | B2 | 8/2006 | Anderson et al. |
| 7,144,401 | B2 | 12/2006 | Yamamoto et al. |
| 7,147,646 | B2 | 12/2006 | Dana et al. |
| 7,153,314 | B2 | 12/2006 | Laufer et al. |
| 7,220,266 | B2 | 5/2007 | Gambale |
| 7,232,445 | B2 | 6/2007 | Kortenbach et al. |
| 7,235,086 | B2 | 6/2007 | Sauer et al. |
| 7,326,221 | B2 | 2/2008 | Sakamoto et al. |
| 7,344,545 | B2 | 3/2008 | Takemoto et al. |
| 7,347,863 | B2 | 3/2008 | Rothe et al. |
| 7,361,180 | B2 | 4/2008 | Saadat et al. |
| 7,530,985 | B2 | 5/2009 | Takemoto et al. |
| 7,601,161 | B1 | 10/2009 | Nobles et al. |
| 7,618,425 | B2 | 11/2009 | Yamamoto et al. |
| 7,713,277 | B2 | 5/2010 | Laufer et al. |
| 7,722,633 | B2 | 5/2010 | Laufer et al. |
| 7,727,246 | B2 | 6/2010 | Sixto, Jr. et al. |
| 7,736,373 | B2 | 6/2010 | Laufer et al. |
| 7,776,057 | B2 | 8/2010 | Laufer et al. |
| 7,776,066 | B2 | 8/2010 | Onuki et al. |
| 7,842,051 | B2 | 11/2010 | Dana et al. |
| 7,846,180 | B2 | 12/2010 | Cerier |
| 7,857,823 | B2 | 12/2010 | Laufer et al. |
| 7,896,893 | B2 | 3/2011 | Laufer et al. |
| 7,918,867 | B2 | 4/2011 | Dana et al. |
| 7,951,157 | B2 | 5/2011 | Gambale |
| 7,992,571 | B2 | 8/2011 | Gross et al. |
| 7,993,368 | B2 | 8/2011 | Gambale et al. |
| 8,016,840 | B2 | 9/2011 | Takemoto et al. |
| 8,021,376 | B2 | 9/2011 | Takemoto et al. |
| 8,057,494 | B2 | 11/2011 | Laufer et al. |
| 8,062,314 | B2 | 11/2011 | Sixto, Jr. et al. |
| 8,066,721 | B2 | 11/2011 | Kortenbach et al. |
| 8,105,355 | B2 | 1/2012 | Page et al. |
| 8,211,123 | B2 | 7/2012 | Gross et al. |
| 8,216,253 | B2 | 7/2012 | Saadat et al. |
| 8,226,667 | B2 | 7/2012 | Viola et al. |
| 8,277,468 | B2 | 10/2012 | Laufer et al. |
| 8,287,554 | B2 | 10/2012 | Cerier et al. |
| 8,287,556 | B2 | 10/2012 | Gilkey et al. |
| 8,308,765 | B2 | 11/2012 | Saadat et al. |
| 8,313,496 | B2 | 11/2012 | Sauer et al. |
| 8,361,089 | B2 | 1/2013 | Chu |
| 8,388,632 | B2 | 3/2013 | Gambale |
| 8,425,555 | B2 | 4/2013 | Page et al. |
| 8,454,631 | B2 | 6/2013 | Viola et al. |
| 8,480,691 | B2 | 7/2013 | Dana et al. |
| 8,540,735 | B2 | 9/2013 | Mitelberg et al. |
| 8,551,120 | B2 | 10/2013 | Gambale |
| 8,585,720 | B2 | 11/2013 | Gross et al. |
| 8,632,553 | B2 | 1/2014 | Sakamoto et al. |
| 8,679,136 | B2 | 3/2014 | Mitelberg |
| 8,709,022 | B2 | 4/2014 | Stone et al. |
| 8,764,771 | B2 | 7/2014 | Chu |
| 8,882,785 | B2 | 11/2014 | DiCesare et al. |
| 8,926,634 | B2 | 1/2015 | Rothe et al. |
| 8,992,570 | B2 | 3/2015 | Gambale et al. |
| 9,011,466 | B2 | 4/2015 | Adams et al. |
| 9,089,325 | B2 | 7/2015 | Mitelberg et al. |
| 9,125,646 | B2 | 9/2015 | Woodard, Jr. et al. |
| 9,198,562 | B2 | 12/2015 | Mitelberg et al. |
| 9,320,515 | B2 | 4/2016 | Dana et al. |
| 9,345,386 | B1 * | 5/2016 | Cheng ................ A61B 1/00135 |
| 9,486,126 | B2 | 11/2016 | West et al. |
| 9,504,465 | B2 | 11/2016 | Chu |
| 9,510,817 | B2 | 11/2016 | Saadat et al. |
| 9,549,728 | B2 | 1/2017 | Chu |
| 9,750,494 | B2 | 9/2017 | Gross et al. |
| 9,788,831 | B2 | 10/2017 | Mitelberg |
| 9,844,366 | B2 | 12/2017 | Woodard, Jr. et al. |
| 9,867,610 | B2 | 1/2018 | Mitelberg et al. |
| 10,045,871 | B2 | 8/2018 | Saadat et al. |
| 10,143,463 | B2 | 12/2018 | Dana et al. |
| 10,194,902 | B2 | 2/2019 | Nobles et al. |
| 10,258,227 | B1 * | 4/2019 | Wilson ................. A61B 1/0684 |
| 10,335,142 | B2 | 7/2019 | Raybin et al. |
| 2002/0107530 | A1 | 8/2002 | Sauer et al. |
| 2003/0204205 | A1 | 10/2003 | Sauer et al. |
| 2004/0002699 | A1 | 1/2004 | Ryan et al. |
| 2004/0138706 | A1 | 7/2004 | Abrams et al. |
| 2005/0033319 | A1 | 2/2005 | Gambale et al. |
| 2005/0250985 | A1 | 11/2005 | Saadat et al. |
| 2006/0282094 | A1 | 12/2006 | Stokes et al. |
| 2007/0225555 | A1 * | 9/2007 | Stefanchik ......... A61B 17/3415 600/104 |
| 2007/0270908 | A1 | 11/2007 | Stokes et al. |
| 2008/0086148 | A1 | 4/2008 | Baker et al. |
| 2009/0177031 | A1 | 7/2009 | Surti et al. |
| 2010/0137681 | A1 | 6/2010 | Ewers et al. |
| 2010/0198006 | A1 | 8/2010 | Greenburg et al. |
| 2012/0158023 | A1 | 6/2012 | Miltelberg et al. |
| 2012/0271327 | A1 | 10/2012 | West et al. |
| 2013/0096581 | A1 | 4/2013 | Gilkey et al. |
| 2013/0261390 | A1 * | 10/2013 | Hirsch ............... A61B 1/00135 600/114 |
| 2013/0267777 | A1 * | 10/2013 | Avitsian ............. A61B 1/00066 600/123 |
| 2013/0304093 | A1 | 11/2013 | Serina et al. |
| 2014/0121457 | A1 | 5/2014 | Mort et al. |
| 2014/0128668 | A1 | 5/2014 | Cox et al. |
| 2015/0025311 | A1 * | 1/2015 | Kadan ................ A61B 1/00105 600/104 |
| 2015/0126983 | A1 | 5/2015 | Alvarado et al. |
| 2016/0045197 | A1 | 2/2016 | Mitelberg et al. |
| 2016/0143512 | A1 * | 5/2016 | Cheng .................... A61B 1/015 600/125 |
| 2017/0007294 | A1 * | 1/2017 | Iwasaka ............. A61B 17/2909 |
| 2017/0042534 | A1 | 2/2017 | Nobles et al. |
| 2017/0086817 | A1 | 3/2017 | Mitelberg |
| 2017/0086818 | A1 | 3/2017 | Mitelberg |

(56) References Cited

U.S. PATENT DOCUMENTS

| | | |
|---|---|---|
| 2017/0119371 A1 | 5/2017 | Mims et al. |
| 2017/0188796 A1* | 7/2017 | Olden ................ A61B 1/00137 |
| 2017/0319197 A1 | 11/2017 | Gross et al. |
| 2017/0333606 A1* | 11/2017 | Manandhar ........ A61B 1/00135 |
| 2018/0042602 A1 | 2/2018 | Mitelberg et al. |
| 2018/0042603 A1 | 2/2018 | Mitelberg et al. |
| 2018/0153381 A1 | 6/2018 | Wei et al. |
| 2018/0221009 A1 | 8/2018 | Mitelberg et al. |
| 2018/0235604 A1 | 8/2018 | Comee et al. |
| 2018/0344501 A1 | 12/2018 | Saadat et al. |
| 2019/0038113 A1* | 2/2019 | Chu .................... A61B 17/221 |
| 2019/0282073 A1* | 9/2019 | Truckai ............... A61B 1/0057 |
| 2020/0046201 A1* | 2/2020 | Ho ....................... A61B 1/005 |

FOREIGN PATENT DOCUMENTS

| | | |
|---|---|---|
| EP | 1520509 A1 | 4/2005 |
| EP | 2108304 A2 | 10/2009 |
| WO | 0189393 A1 | 11/2001 |
| WO | 2008016592 A2 | 2/2008 |
| WO | 2008045376 A2 | 4/2008 |
| WO | 2008098124 A1 | 8/2008 |
| WO | 2010036227 A1 | 4/2010 |
| WO | 2016200811 A1 | 12/2016 |
| WO | 2017087856 A1 | 5/2017 |
| WO | 2018156603 A1 | 8/2018 |

OTHER PUBLICATIONS

International Search Report and Written Opinion dated Oct. 1, 2019 for International Application No. PCT/US2019/038006.
International Search Report and Written Opinion dated Dec. 6, 2019 for International Application No. PCT/US2019/037995.
Invitation to Pay Additional Fees dated Sep. 26, 2019 for International Application No. PCT/US2019/037995.
International Search Report and Written Opinion dated Nov. 18, 2019 for International Application No. PCT/US2019/049774.
International Search Report and Written Opinion dated Sep. 20, 2019 for International Application No. PCT/US2019/039312.

* cited by examiner

ENDOSCOPIC HANDLE ATTACHMENT FOR USE WITH SUTURE BASED CLOSURE DEVICE

CROSS-REFERENCE TO RELATED APPLICATIONS

This application claims the benefit of priority under 35 U.S.C. § 119 of U.S. Provisional Application No. 62/848,853 filed May 16, 2019; U.S. Provisional Application No. 62/794,075, filed Jan. 18, 2019; and U.S. Provisional Application No. 62/686,923, filed Jun. 19, 2018, the entire disclosures of which are hereby incorporated by reference.

TECHNICAL FIELD

The disclosure is directed to devices for use with endoscopes and more particularly to devices that work with an endoscope or similar device for endoscopically suturing tissue.

BACKGROUND

A variety of endoscopic treatments may result in defects (or wounds) that are too large for hemostasis clips to easily bridge and thus help to close the defect. Examples of such endoscopic treatments include removal of large lesions, tunneling under the mucosal layer, full thickness removal of tissue, treating other organs by passing outside of the gastrointestinal tract, and repair of post-surgical issues such as post-surgical leaks, failing surgical staple lines and anastomotic leaks. Endoscopic treatments also include bariatric revision procedures. Of the known devices and methods for endoscopically closing large defects, each has certain advantages and disadvantages.

SUMMARY

The disclosure is directed to several alternative designs, materials and methods of devices for endoscopically closing large defects. An example of the disclosure is an endoscopic handle attachment that is adapted to be secured to an endoscope having a working channel and used in combination with a suture device adapted to extend through the working channel, the suture device including a translation assembly axially translatable within the working channel and adapted to releasably engage and disengage a needle and a distal endcap securable to the distal end of the endoscope and adapted to releasable engage the needle when the translation assembly disengages the needle and to disengage the needle when the translation assembly engages the needle, the suture device including a proximal handle and a translation handle slidingly coupled to the proximal handle and operably coupled to the translation assembly such that movement of the translation handle relative to the proximal handle causes movement of the translation assembly. The endoscopic handle attachment includes a backbone that is adapted to conform to an outer surface of the endoscope and that includes one or more attachment features that are adapted to enable the endoscopic handle attachment to be releasably secured to the endoscope proximate a handle region of the endoscope. A primary arm extends radially outwardly from the backbone and one or attachment members are coupled to the primary arm, at least one of the one or more attachment members adapted to releasably secure the proximal handle of the suture device such that the translation handle may be moved relative to the proximal handle without an operator needing to separately hold the proximal handle.

Alternatively or additionally, the one or more attachment features may include hook structures that are formed into the backbone and are adapted to secure one or more elastic members that engage the hook structures and extend around the endoscope.

Alternatively or additionally, the hook structures may include a first hook on a first side of the backbone and an opposing second hook on a second side of the backbone.

Alternatively or additionally, the primary arm may include a first attachment member adapted to releasably secure the proximal handle of the suture device and a second attachment member adapted to releasably secure a handle for a secondary device used in combination with the suture device.

Alternatively or additionally, the first attachment member may include a C-shaped attachment member into which the proximal handle of the suture device is releasably engageable via a snap fit.

Alternatively or additionally, the endoscopic handle attachment may further include a secondary arm having an attachment member adapted to releasably secure an external lumen used with the suture device.

Alternatively or additionally, the attachment member of the secondary arm may include an aperture extending through the attachment member such that a fitting of the external lumen may be extended upwardly through the aperture and a valve may be extended down into the aperture to engage the fitting and thus releasably secure the external lumen to the attachment member of the secondary arm.

Alternatively or additionally, the secondary device may be adapted to extend from the handle releasably secured to the second attachment member of the primary arm and into the external lumen releasably secured to the attachment member of the secondary arm.

Alternatively or additionally, the endoscope may include an instrument channel port that is fluidly coupled with the working channel, and the backbone may include an upper portion adapted to fit about an instrument channel port bump out accommodating the instrument channel port.

Alternatively or additionally, the upper portion adapted to fit about the instrument channel port bump out may include one or more tabs adapted to contact the instrument channel port bump out and thus vertically position the endoscopic handle attachment relative to the instrument channel port.

Another example of the disclosure is an endoscopic handle attachment that is adapted to be secured to an endoscope having a working channel and used in combination with a suture device adapted to extend through the working channel, the suture device including a translation assembly axially translatable within the working channel and a distal assembly and adapted to pass a needle back and forth between the translation assembly and the distal assembly, the suture device including a proximal handle and a translation handle slidingly coupled to the proximal handle and operably coupled to the translation assembly. The endoscopic handle attachment includes a backbone that is adapted to conform to an outer surface of the endoscope and that includes one or more attachment features that are adapted to enable the endoscopic handle attachment to be releasably secured to the endoscope proximate a handle region of the endoscope. A primary arm extends radially outwardly from the backbone and a suture device attachment member is coupled to the primary arm and adapted to releasably secure the proximal handle of the suture device such that the translation handle may be moved relative to the proximal handle without an operator needing to separately hold the proximal handle. A secondary device attachment member is coupled to the primary arm and adapted to releasably engage a handle of a secondary device adapted to be used in combination with the suture device.

Alternatively or additionally, the endoscopic handle attachment further includes a secondary arm extending radially outwardly from the backbone and including an external lumen attachment member, the external lumen attachment member including an aperture extending through the external lumen attachment member such that a fitting of the external lumen may be extended upwardly through the aperture and a valve may be extended down into the aperture to engage the fitting and thus releasably secure the external lumen to the external lumen attachment member.

Alternatively or additionally, the one or more attachment features may include hook structures that are formed into the backbone and are adapted to secure one or more elastic members that engage the hook structures and extend around the endoscope.

Alternatively or additionally, the hook structures may include a first hook on a first side of the backbone and an opposing second hook on a second side of the backbone.

Alternatively or additionally, the suture device attachment member may be adapted to releasably engage the proximal handle of the suture device via a snap fit.

Alternatively or additionally, the secondary device attachment member may be adapted to releasably engage the handle of the secondary device via a snap fit.

Alternatively or additionally, the endoscope includes an instrument channel port that is fluidly coupled with the working channel, and the backbone may include an upper portion adapted to fit about an instrument channel port bump out accommodating the instrument channel port, the upper portion including one or more tabs adapted to contact the instrument channel port bump out and thus vertically position the endoscopic handle attachment relative to the instrument channel port.

Another example of the disclosure is a suture assembly for use in combination with an endoscope having a working channel and a distal end. The suture assembly includes a translation assembly that is axially translatable within the working channel and includes a needle configured to carry a suture, a distal shuttle configured to releasably secure the needle and a sleeve disposable over the distal shuttle, the sleeve movable between a locked position in which the needle is secured to the distal shuttle and an unlocked position in which the needle is releasable from the distal shuttle. The suture assembly includes a distal endcap that is securable to the distal end of the endoscope and is configured to engage the needle when the needle is advanced distally into the endcap and to release the needle when the needle is locked to the distal shuttle and the distal shuttle is withdrawn proximally. The suture assembly includes a proximal handle and a translating handle that is slidingly disposed relative to the proximal handle and is operably coupled to the translation assembly. A backbone is adapted to conform to an outer surface of the endoscope and to be releasably secured to the endoscope proximate an instrument channel port of the endoscope. An arm extends radially outwardly from the backbone and a suture assembly attachment member is coupled to the arm and is adapted to releasably secure the proximal handle such that the translation handle may be moved relative to the proximal handle without an operator needing to separately hold the proximal handle.

Alternatively or additionally, the suture assembly may further include a secondary device attachment member coupled to the arm for securing a handle of a secondary device used in combination with the suture assembly.

Alternatively or additionally, the suture assembly may further include a second arm bearing an external lumen attachment member.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE FIGURES

The disclosure may be more completely understood in consideration of the following description of in connection with the accompanying drawings, in which.

Figure 1:
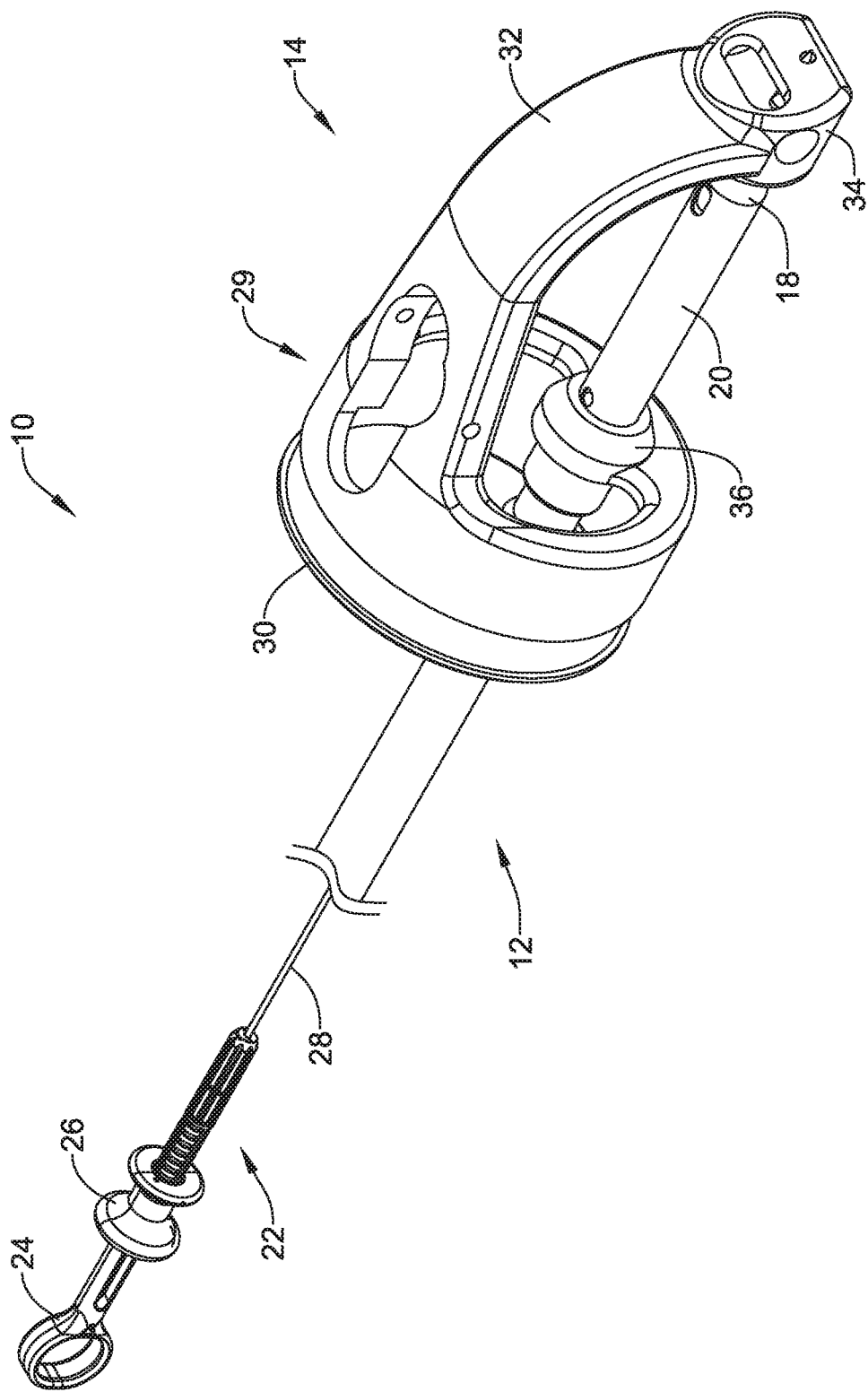
FIG. 1 is a perspective view of an illustrative suture device in accordance with an example of the disclosure.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

The disclosure pertains to devices that are configured to be used in combination with an endoscope or a similar delivery device for closing wounds within the body. In some instances, the suture devices described herein may be configured such that they may be used within a single working or available channel of an endoscope, and in some cases may be operated by a single individual, although in some cases a second individual may be involved. In some cases, the suture devices described herein may be considered as operating along a single line of operation. The device itself may be translatable distally and proximally within a working channel, and a handle portion may itself be translatable distally and proximally along the same line of operation in locking and unlocking a needle to be able to pass the needle back and forth between an active portion of the suture device and a passive portion of the suture device. The device may be configured to enable the needle to be selectively locked into either of a more distal position or a more proximal position, and the device may itself be translated distally or proximally with the needle locked in place in order to move the needle, and hence a suture, relative to the tissue being repaired.

FIG. 1 is a perspective view of a suture device 10 that may be considered as being configured for use in combination with a delivery system including a lumen that extends through the delivery system. For example, the delivery system may be an endoscope having a working channel. The delivery system may also be a catheter. It will be appreciated that there is a change in scale on either side of the break line shown. In some cases, the suture device 10 may be considered as including a suture translation assembly 12 that is configured to be axially translatable within the lumen of the delivery system and a distal assembly 14 that is configured to be secured to a distal end of the delivery system. The suture translation assembly 12 extends into the distal assembly 14 and includes a needle 16 that may be used to carry a suture as well as a distal shuttle 18 that is configured to releasably secure the needle 16.

A member 20 may be disposed over the distal shuttle 18 and, as will be shown in subsequent Figures, is movable between a locked position in which the needle 16 is secured to the distal shuttle 18 and an unlocked position in which the needle 16 is releasable from the distal shuttle 18. In some cases, for example, the member 20 may be a sleeve 20. A user interface 22 extends proximally from the distal shuttle 18 and the sleeve 20, and may be configured to move the sleeve 20 between the locked position and the unlocked position. In some cases, as shown, the user interface 22 may include a proximal handle 24 and a translating handle 26 that is disposed relative to the proximal handle 24. In some cases, as will be described, the proximal handle 24 may be used to move the suture device 10 proximally or distally, while the translating handle 26 may be used to move the needle 16 between the distal shuttle 18 and the distal assembly 14. A shaft 28 may extend distally from the proximal handle 24 to the suture translation assembly 12, and may in particular be coupled to the sleeve 20.

In some cases, the distal assembly 14 includes a body 29 having a proximal connector 30 that may be configured to be coupled to the distal end of an endoscope or other delivery system. The body 29 includes an arm 32 that extends to an endcap 34. As will be discussed, the endcap 34 may be configured to releasably engage and disengage the needle 16. In some cases, for example, the endcap 34 may be configured to engage the needle 16 when the needle 16 is advanced distally into the endcap 34, and to release the needle 16 when the needle 16 is locked into the distal shuttle 18 (as will be discussed) and the distal shuttle 18 is withdrawn proximally. The distal assembly 14 may be considered as including a guide member 36 that may be secured to or integrally formed with the body 29, and may permit the suture translation assembly 12 to extend through the guide member 36 and to translate relative to the guide member 36. In some cases, the body 29 may include an aperture 27 that may enable other devices to be inserted through the aperture 27. In some instances, as will be discussed with respect to subsequent Figures, the aperture 27 may be configured to accommodate a side-saddled lumen attachment element. In some cases, the aperture 27 may include one or more of a pin aperture 31a and a pin aperture 31b that may, for example, be used to mount the aforementioned side-saddled lumen attachment element, or possibly other features as well.

Figure 2:
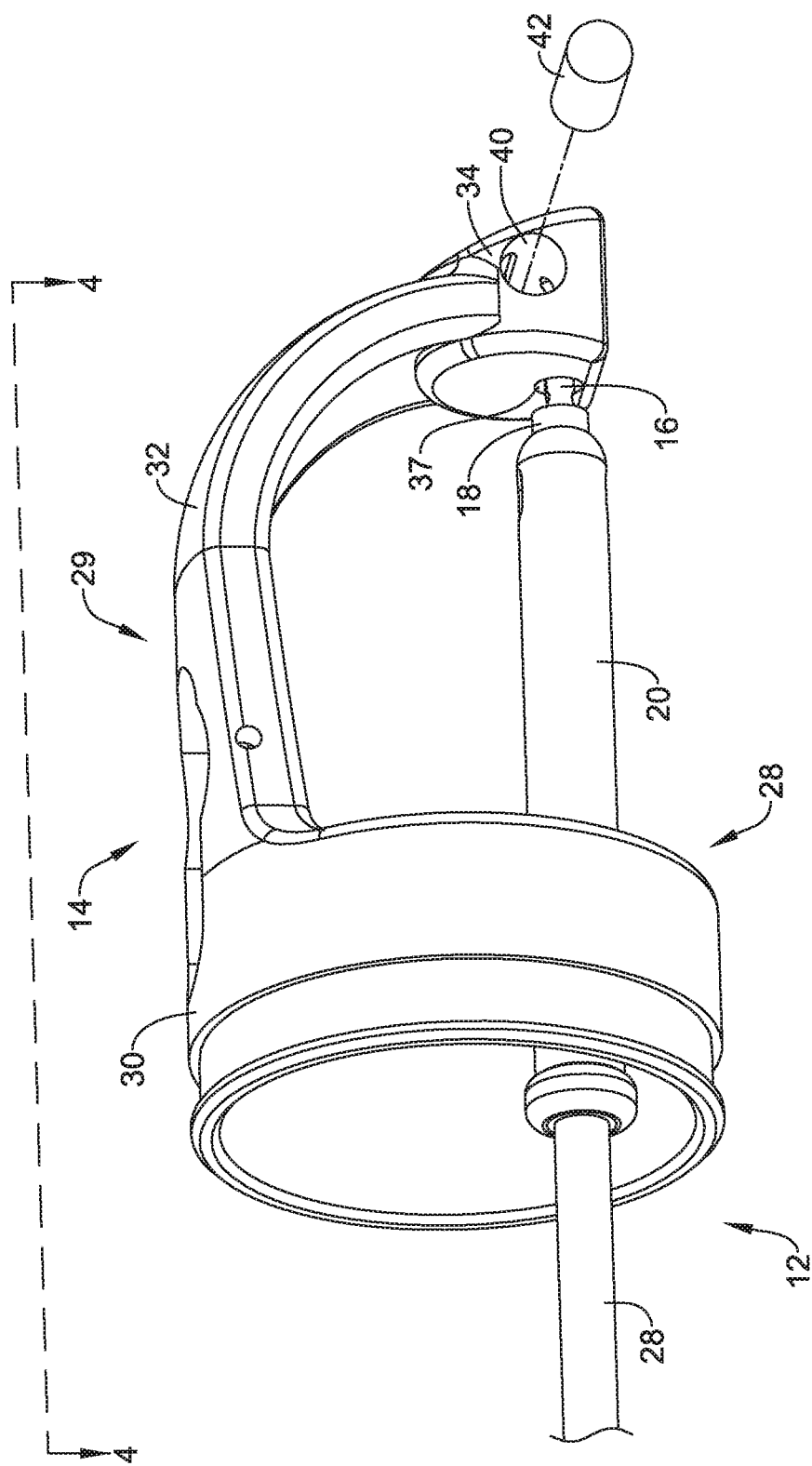
FIG. 2 is a perspective view of a distal assembly forming part of the illustrative suture device of FIG. 1, shown in an extended position.
Figure 3:
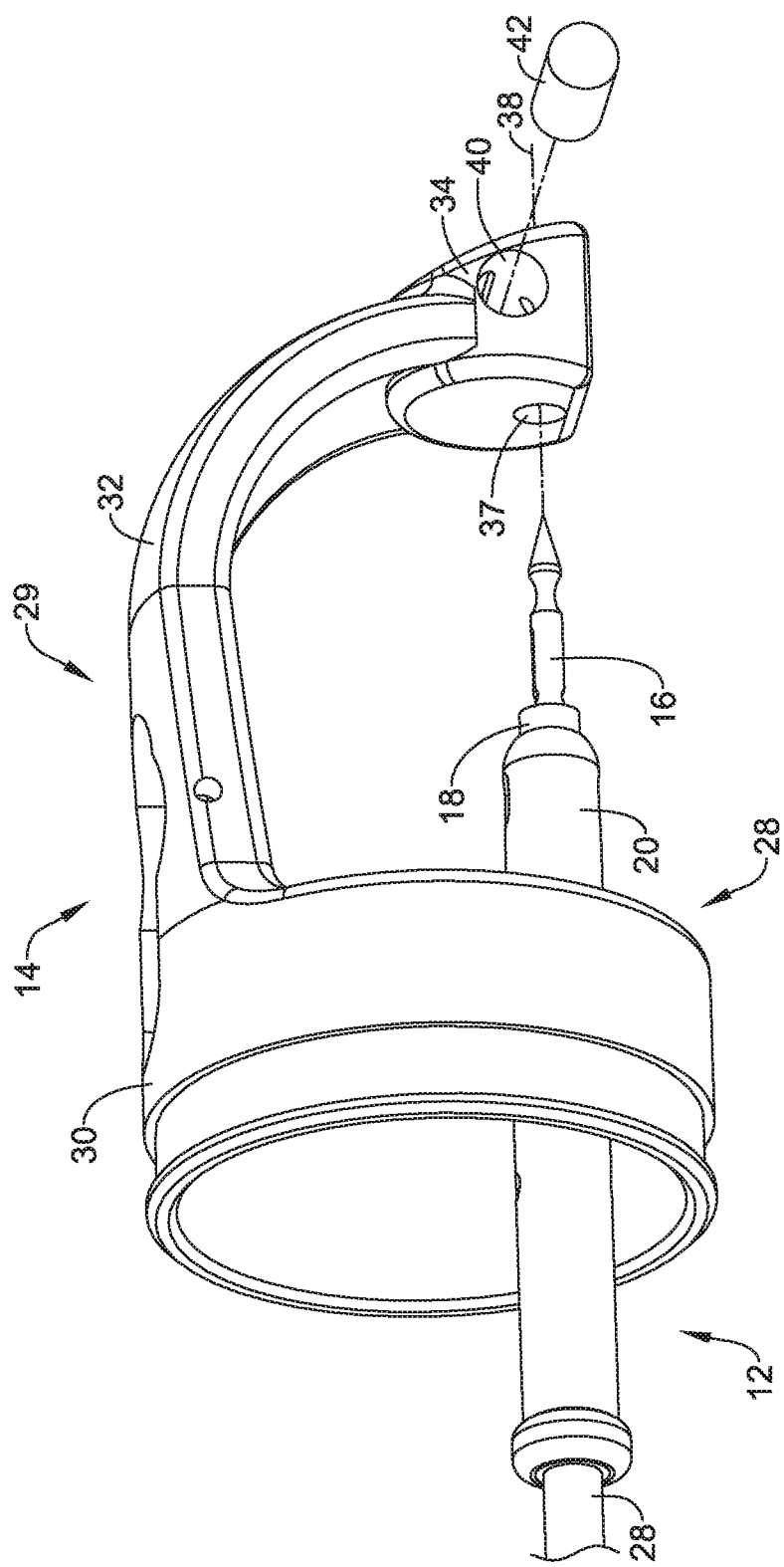
FIG. 3 is a perspective view of the distal assembly of FIG. 2, shown in a retracted position.

FIG. 2 and FIG. 3 show the suture translation assembly 12 extended through the guide member 36 and into the distal assembly 14. In FIG. 2, the suture translation assembly 12 is shown in an extended position in which the needle 16 extends into the endcap 34 while in FIG. 3, the suture translation assembly 12 is shown in a retracted position in which the needle 16 has been withdrawn proximally from the endcap 34. In some cases, as can be seen, the endcap 34 includes a proximal needle opening 36 that is configured to help guide the needle 16 into the proximal needle opening 36 as well as to accommodate the needle 16 when the needle 16 is advanced distally into the endcap 34. In some cases, the proximal needle opening 36 may extend all the way through the endcap 34 while in other cases the proximal needle opening 36 may not pass all the way through the endcap 34. In some instances, as shown, the proximal needle opening 36 may be considered as being aligned with a longitudinal axis 38 of the needle 16 (as shown in FIG. 3).

One or more securement openings 40 may be arranged orthogonal to the proximal needle opening 36 and one or more securements 42 that are configured to be disposed within the one or more securement openings 40, and which are configured to releasably engage the distal detent (as will be discussed) of the needle 16. In some cases, there may be a pair of securement openings 40, one on either side of the endcap 34. In some cases, there may be a pair of securements 42, with one disposed within each of the pair of securement openings 40. In some cases, while shown schematically, the one or more securements 42 may be springs or coils, for example.

Figure 4:
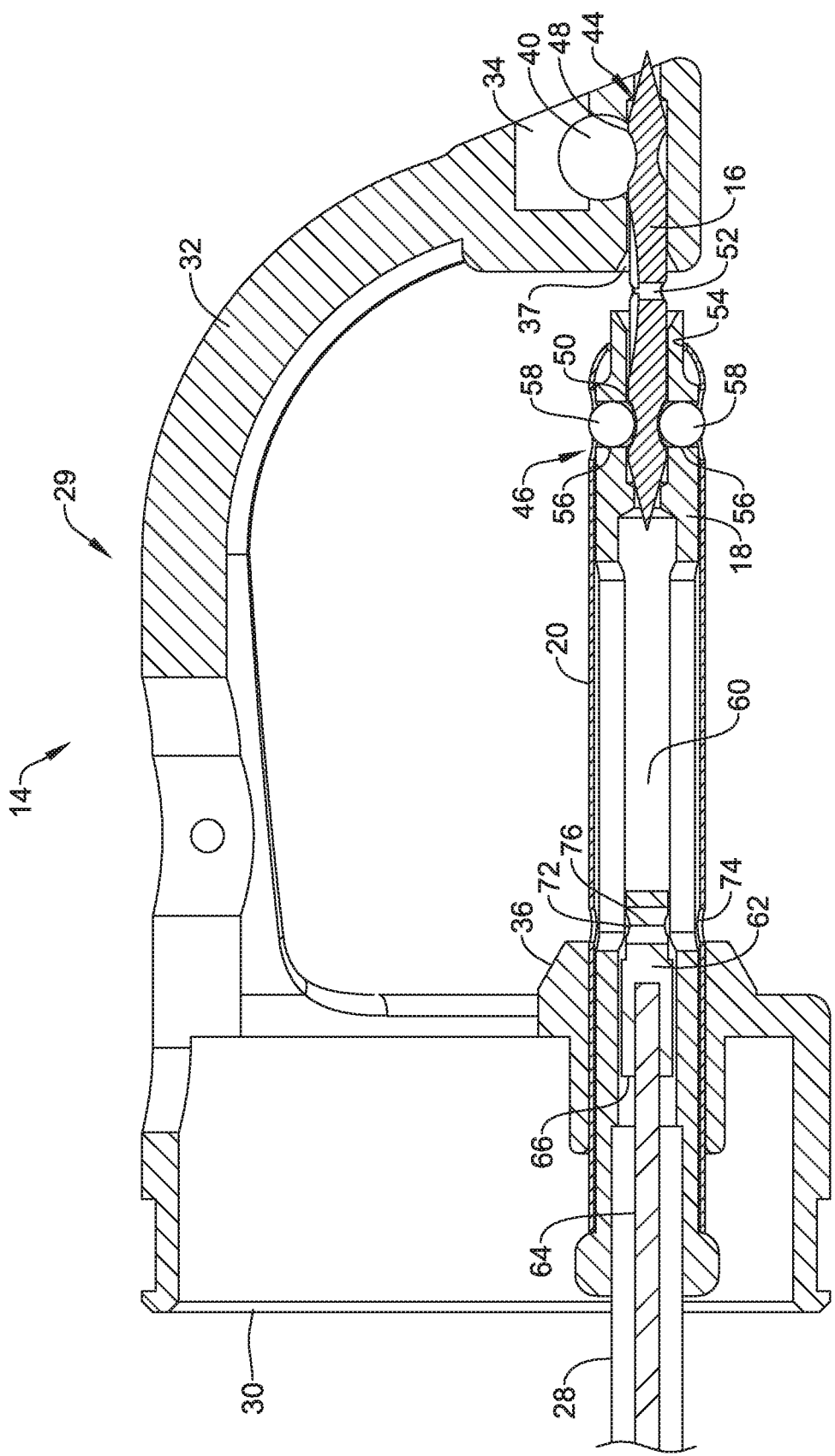
FIG. 4 is a cross-sectional view of the distal assembly of FIG. 2, taken along the line 4-4.
Figure 5:
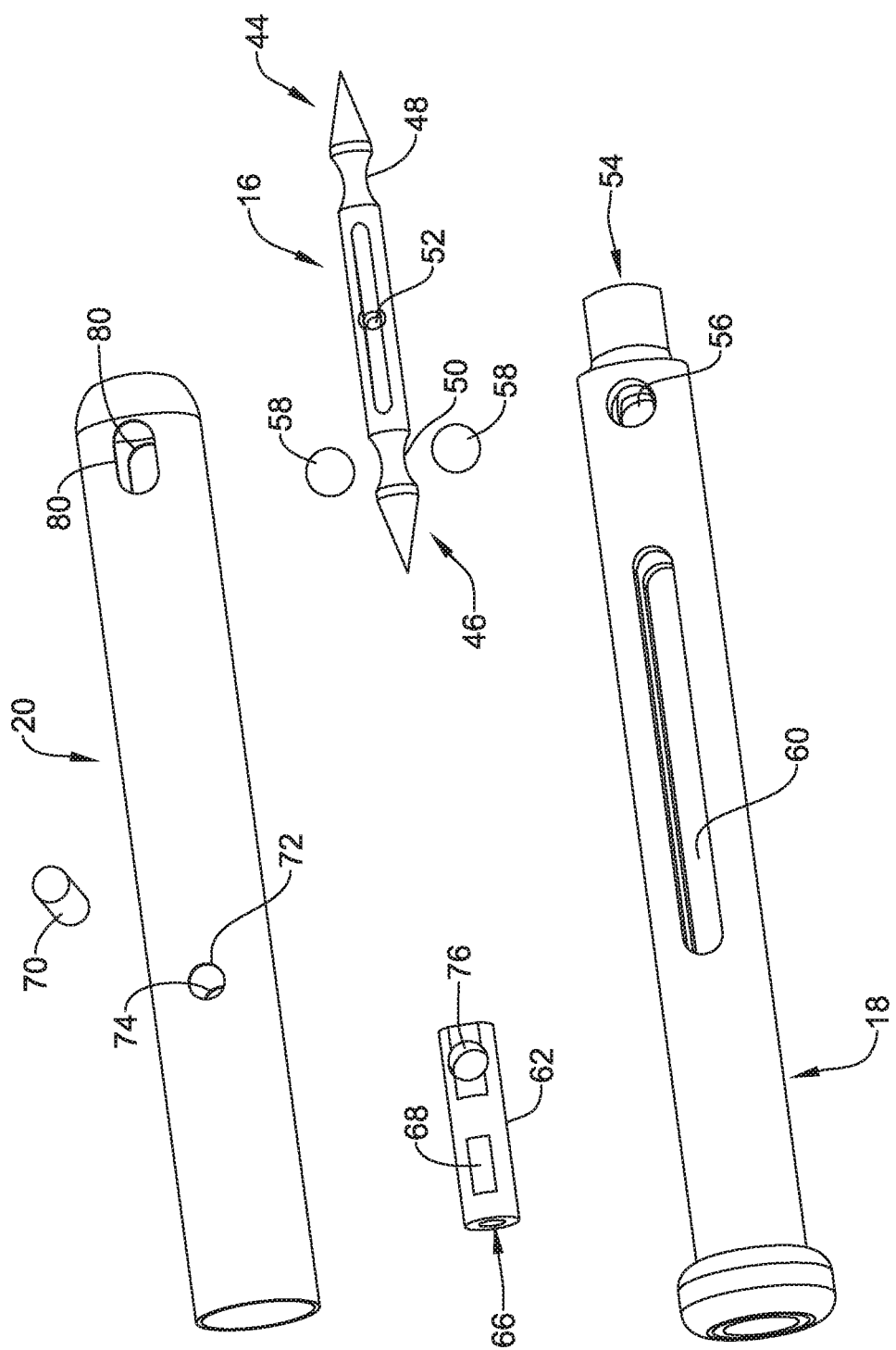
FIG. 5 is an exploded view of a portion of a suture translation assembly forming part of the illustrative suture device of FIG. 1.

FIG. 4 is a cross-sectional view of the distal assembly 14, with the suture translation assembly 12 disposed within the distal assembly 14. FIG. 5 is an exploded view of the suture translation assembly 12. The needle 16 may be considered as including a distal region 44 and a proximal region 46. In some cases, the distal region 44 may include a distal detent 48 for releasably engaging the endcap 34 and the proximal region 46 may include a proximal detent 50 for releasably engaging the distal shuttle 18. The needle 16 may, as shown, include an aperture 52 for accommodating a suture line passing therethrough.

In some cases, the distal shuttle 18 may be considered as including a distal needle opening 54 that is configured to accommodate the needle 16 when the distal shuttle 18 is advanced distally over the needle 16 and that is aligned with the longitudinal axis 38 of the needle 16. One or more bearing ball openings 56 may be arranged orthogonal to the distal needle opening 54 such that the one or more bearing ball openings 56 align with the proximal detent 50 when the needle 16 is secured to the distal shuttle 18. In some cases, one or more bearing balls 58 may be disposed within the one or more bearing ball openings 56 and may be configured to be disposed within the proximal detent 50 when the needle 16 is secured to the distal shuttle 18.

In some cases, the distal shuttle 18 includes an internal void 60 and a sleeve capture member 62 that is slidingly disposed within the internal void 60. In some cases, the sleeve capture member 62 may be coupled to a cable 64 extending distally from the user interface 22 within the shaft 28 and into a cable aperture 66 and secured via a crimp or other mechanical connection 68. In some cases, the sleeve capture member 62 may be coupled to the sleeve 20 via a pin 70 that extends through first and second sleeve connection apertures 72, 74 and a corresponding aperture 76 extending through the sleeve capture member 62 as well as extending through the internal void 60. As the cable 64 is operably coupled to the translating handle 26 (as will be discussed), it will be appreciated that moving the translating handle 26 distally or proximally relative to the proximal handle 24 causes a corresponding distal or proximal movement of the sleeve 20 relative to the distal shuttle 18.

In some cases, the sleeve 20 includes one or more sleeve openings 80 that may be smaller in diameter, or smaller in width, than the diameter of the one or more bearing balls 58. In some cases, the sleeve 20 may include a pair of sleeve openings 80, corresponding to a pair of bearing ball openings 56 and a pair of bearing balls 58. When the sleeve 20 is in the locked position, as shown for example in FIG. 6A, the one or more sleeve openings 80 are misaligned with, or do not align with, the one or more bearing ball openings 56, and so the one or more bearing balls 58 engage the proximal detent 50 of the needle 16. The sleeve 20 prevents the one or more bearing balls 58 from being pushed out of the proximal detent 50.

Figure 6A:
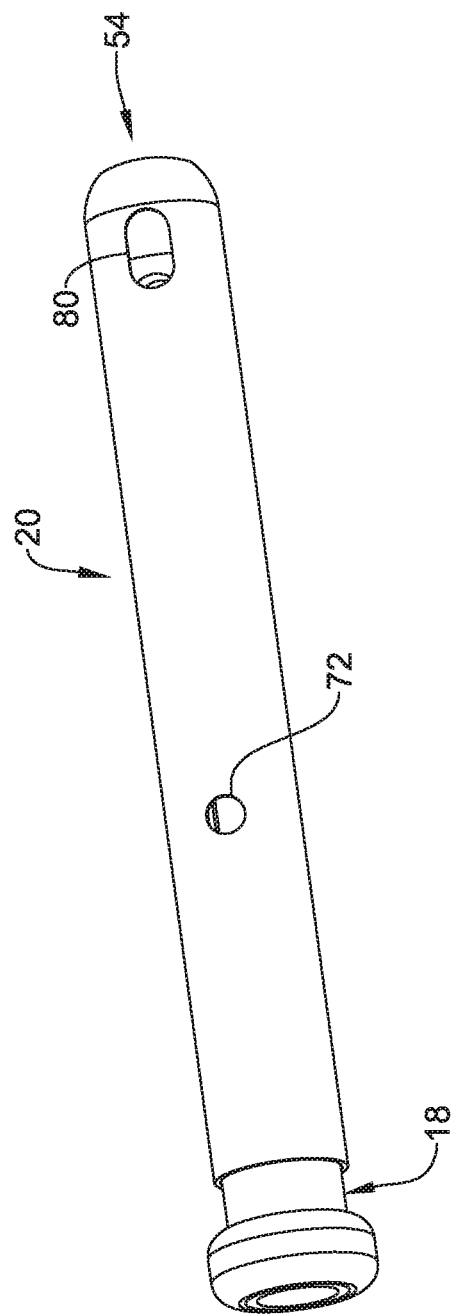
FIG. 6A is a side view of a distal shuttle and a member forming part of the suture translation assembly, with the member shown extended in a locked position.
Figure 6B:
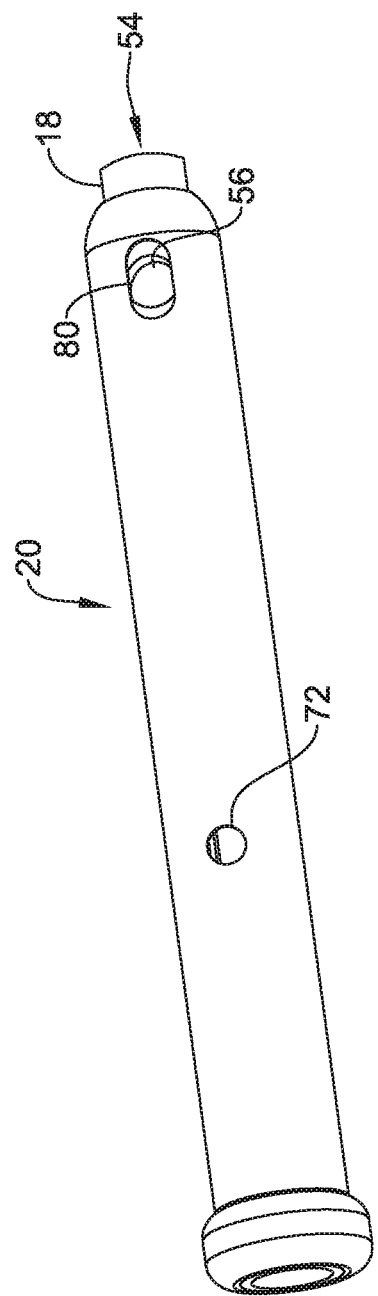
FIG. 6B is a side view of the distal shuttle and the member of FIG. 6A, with the member shown retracted in an unlocked position.

Conversely, when the sleeve 20 is in the unlocked position, as shown for example in FIG. 6B, the one or more sleeve openings 80 are aligned with the one or more bearing ball openings 56. This permits the one or more bearing balls 58 to move radially out, into the one or more sleeve openings 80, a distance sufficient to permit the one or more bearing balls 58 to clear the proximal detent 50 of the needle 16 in response to a force applied to the one or more bearing balls 58 by the needle 16. With reference to FIG. 4, while the suture translation assembly 12 is shown advanced into the distal assembly 14, the sleeve 20 is in the unlocked position relative to the distal shuttle 18, and thus the one or more bearing balls 58 may be seen as extending partially into the one or more sleeve openings 80.

In some cases, it will be appreciated that the distal shuttle 18, and the sleeve 20, in combination, provide an active connection to the needle 16 while the distal endcap 34 provides a passive connection to the needle 16. If the needle 16 is moved distally into the distal endcap 34, the distal endcap 34 will grab onto the needle 16, with the one or more securements 42 engaging the distal detent 48. If the needle 16 is subsequently moved proximally, the axial force applied overcomes any resistance provided by the one or more securements 42, and the needle 16 is able to move proximally. In contrast, the active connection to the needle 16 provided by the distal shuttle 18 and the sleeve 20, however, requires action to move the sleeve 20, relative to the distal shuttle 18, between the locked position and the unlocked position. The user interface 22 provides a mechanism for positively moving the sleeve 20 between the locked and unlocked positions.

Figure 7:
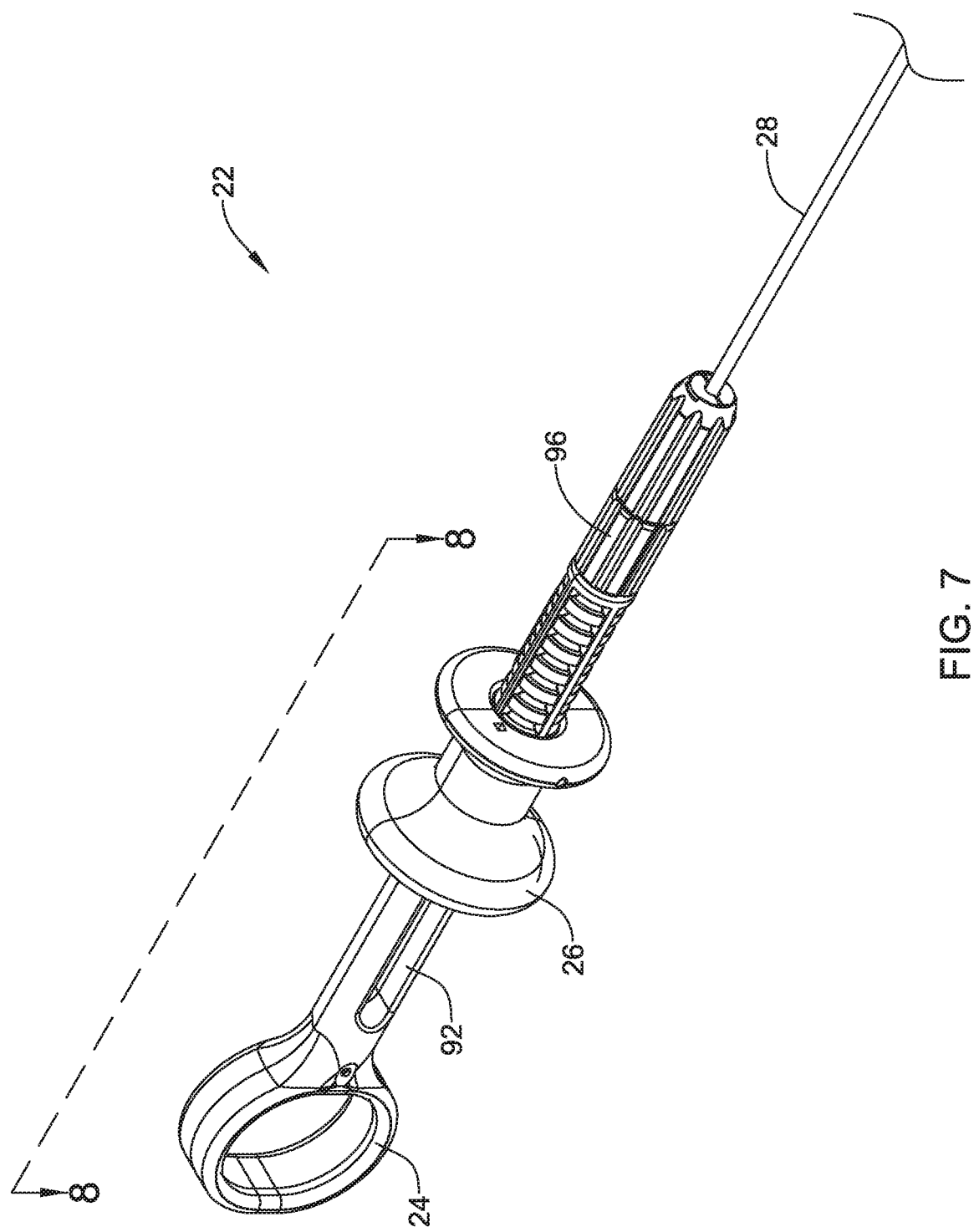
FIG. 7 is a perspective view of a handle portion of a suture translation assembly forming part of the illustrative suture device of FIG. 1.
Figure 8:
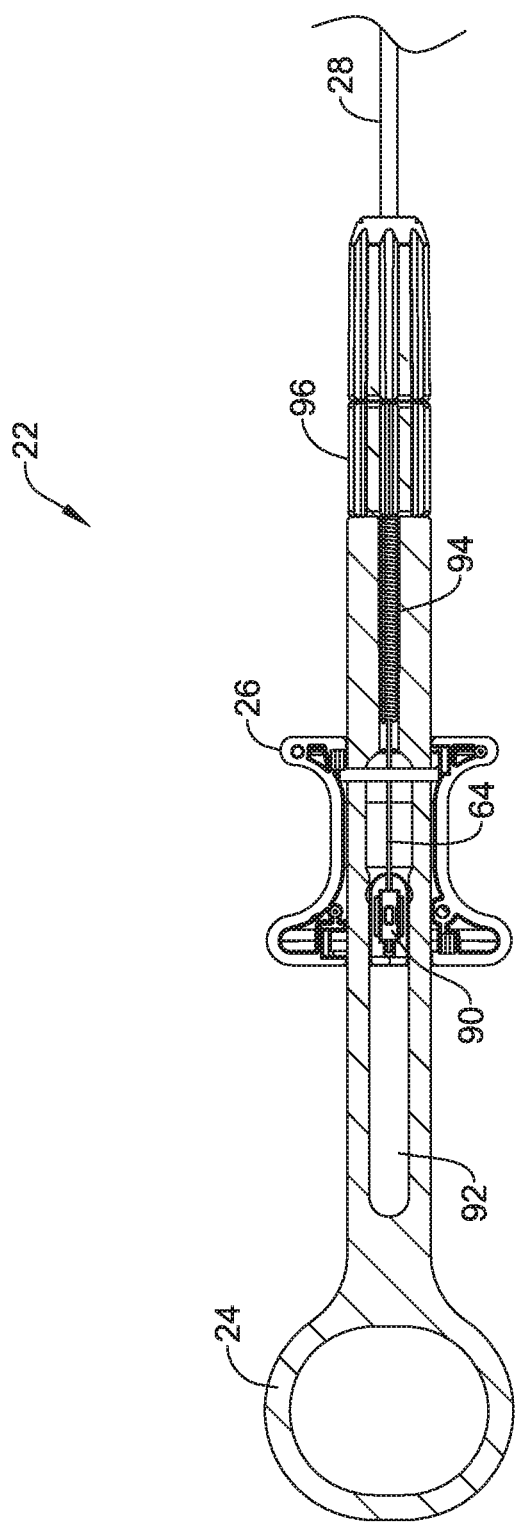
FIG. 8 is a cross-sectional view of the handle portion of FIG. 7, taken along the line 8-8.

FIG. 7 is a perspective view of the user interface 22 and FIG. 8 is a cross-sectional view along line 8-8 of FIG. 7. The cable 64, which extends through the shaft 28, is coupled to the translating handle 26 via a connector 90. The connector 90 is able to translate relative to the proximal handle 24, and thus enable the translating handle 26 to translate relative to the proximal handle 24, by translating within a void 92 formed within the proximal handle 24. In some cases, the shaft 28 includes a coil 94. It will be appreciated that the relative position of the translating handle 26 (relative to the proximal handle 24) shown in FIGS. 7 and 8 corresponds to the sleeve 20 being in the locked position (as shown in FIG. 6A). In some cases, the proximal handle 24 includes a handle portion 96.

Figure 9A:
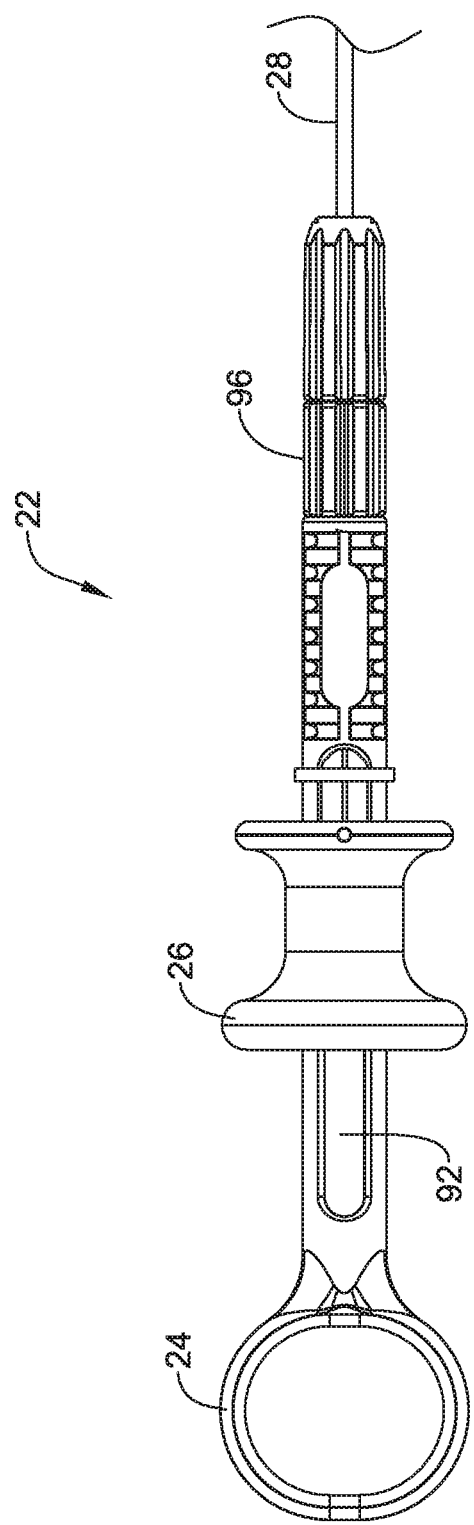
FIG. 9A is a perspective view of the handle portion of FIG. 7, shown in an intermediate position.
Figure 9B:
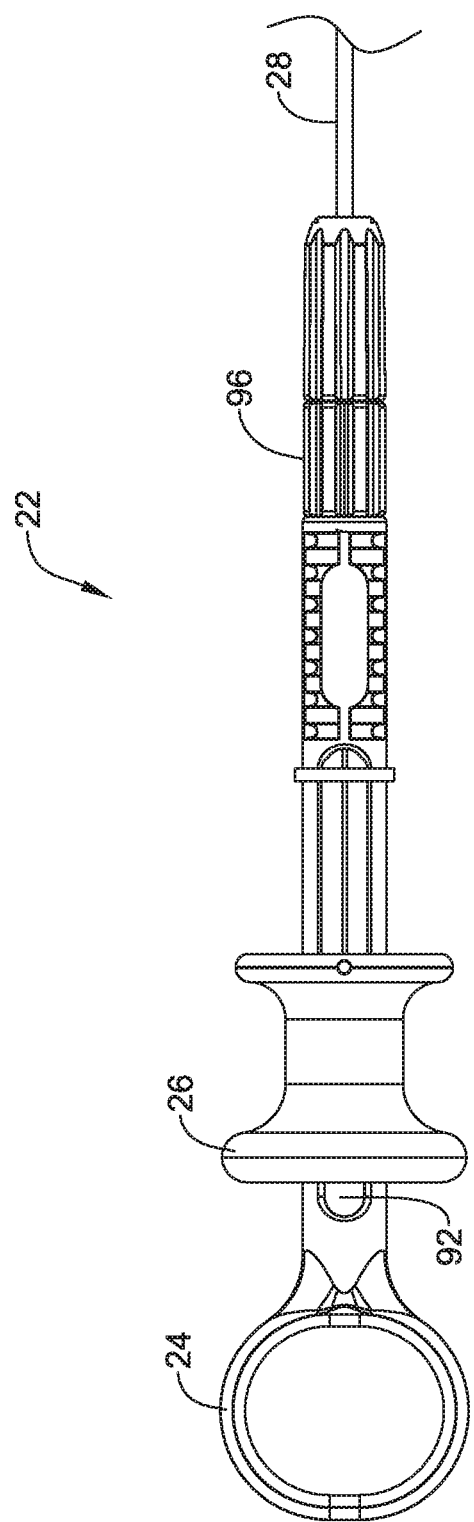
FIG. 9B is a perspective view of the handle portion of FIG. 8, shown in a retracted, unlocked position.

FIG. 9A is a perspective view of the user interface 22 with the translating handle 26 shown in an intermediate position relative to the proximal handle 24 while FIG. 9B is a perspective view of the user interface 22 with the translating handle 26 shown in a retracted, unlocked position. Accordingly, to move the sleeve 20 into the locked position, a user may move the translating handle 26 distally relative to the proximal handle 24, from the neutral position. To move the sleeve 20 into the unlocked position, a user may move the translating handle 26 proximally relative to the proximal handle 24, from the neutral position. In some cases, a user has to intentionally engage the translating handle 26 in order to lock or unlock the needle 16 relative to the distal shuttle 18.

Additional features of the suture device 10, including the suture translation assembly 12, the distal assembly 14, the proximal handle 24 and the translating handle 26, may be found in U.S. patent application Ser. No. 15/901,477 entitled SUTURE BASED CLOSURE DEVICE, which application was filed on Feb. 21, 2018 and which application is hereby incorporated by reference herein in its entirety. As noted, the suture device 10 may be used in combination with an endoscope. In some cases, a user of the suture device 10 may have need to control various features of the endoscope as well as manipulating the proximal handle 24 and/or the translating handle 26 while endoscopically suturing tissue, as described in the aforementioned U.S. Ser. No. 15/901,477

Figure 10:
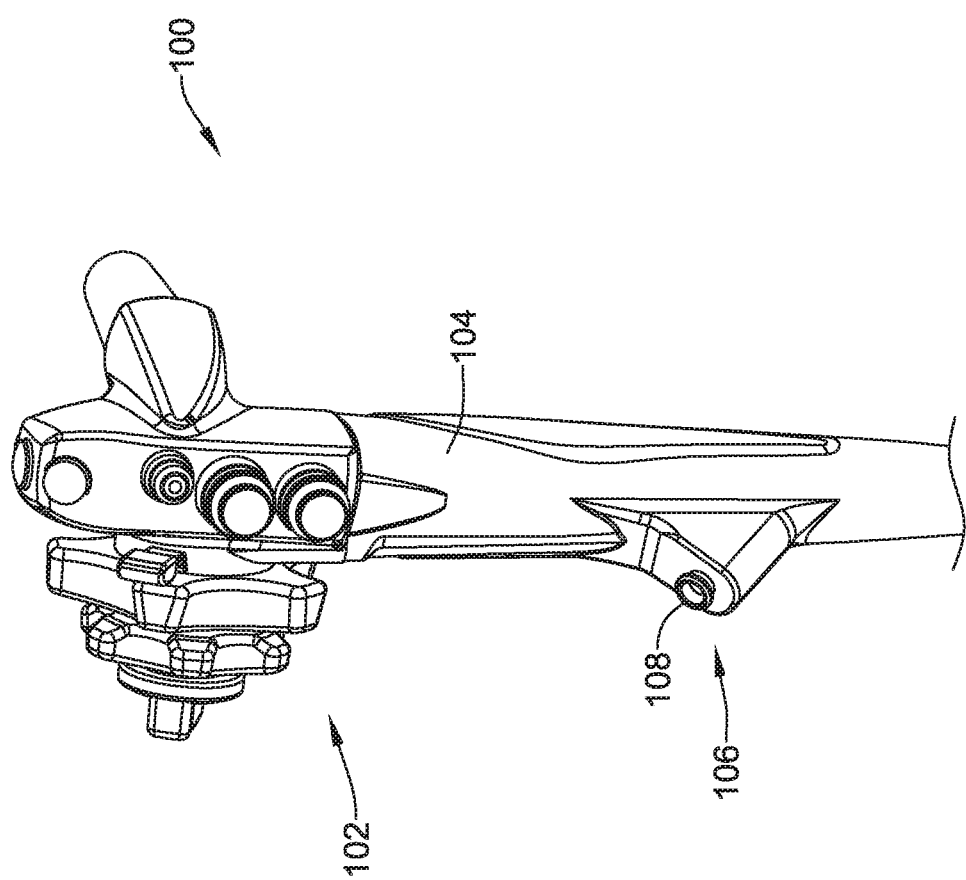
FIG. 10 is a perspective view of a proximal portion of an illustrative endoscope with which the illustrative suture device of FIG. 1 may be used in accordance with an example of the disclosure.

FIG. 10 is a perspective view of the proximal portion of an endoscope 100. Certain features of the endoscope 100 as illustrated, such as particular features and elements of a handle portion 102, are merely illustrative, and are not intended to be limiting in any way. The endoscope 100 includes an outer surface 104 that in some cases, as shown, may taper away from the handle portion 102. The endoscope 100 may include an instrument channel port bump out 106 that accommodates an instrument channel port 108. It will be appreciated that being able to position the proximal handle 24 and the translating handle 26 near the handle portion 102 of the endoscope 100 may be beneficial.

Figure 11:
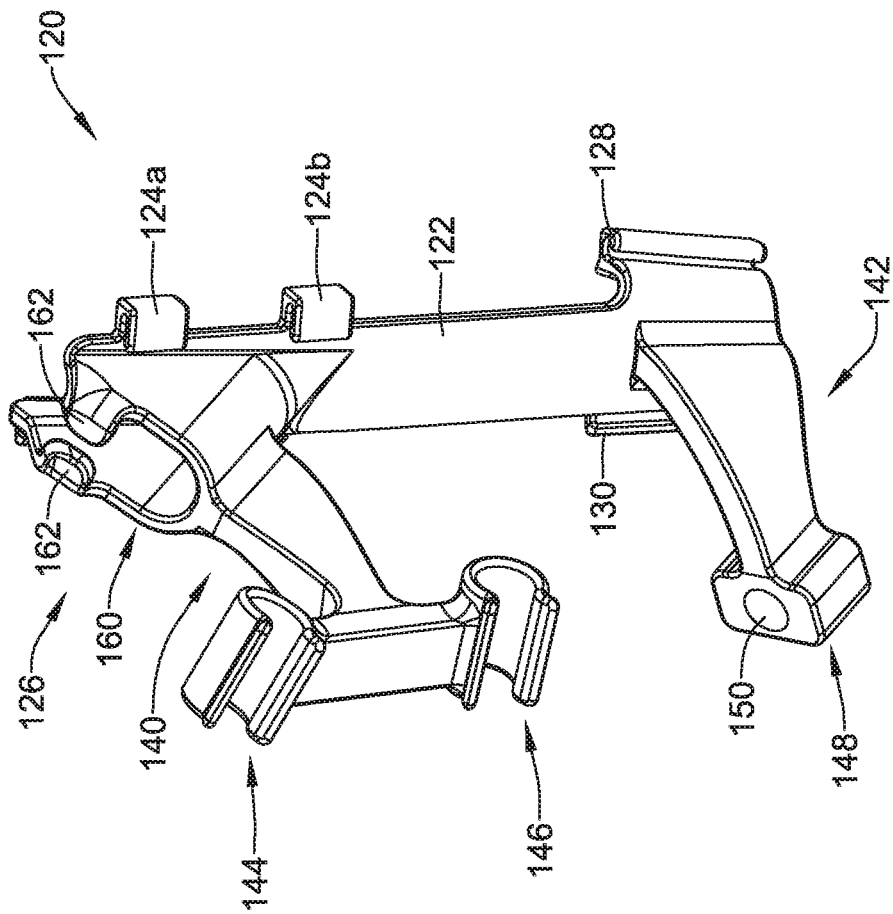
FIG. 11 is a perspective view of an endoscope attachment mechanism that may be used with the illustrative suture device of FIG. 1 and the illustrative endoscope of FIG. 10 in accordance with an example of the disclosure.

FIG. 11 is a perspective view of an endoscope handle attachment 120 that may, as will be shown, be configured to be releasably secured to the endoscope 100, such as near the handle portion 102 of the endoscope 100. The endoscope handle attachment 120 includes a backbone 122 that is adapted to conform to the outer surface 104 of the endoscope 100, or to the outer surface of any other non-illustrated endoscope. In some cases, the backbone 122 may be straight in order to accommodate an outer surface of an endoscope. In some instances, the backbone 122 may be curved in one or more dimensions in order to accommodate an outer surface of an endoscope. In some cases, the backbone 122 may curve sufficiently around the outer surface 104 of the endoscope 100 such that the endoscope handle attachment 120 may simply fit onto the endoscope 100 via a snap fit.

In some cases, the backbone 122 may include one or more attachment features that are adapted to enable the endoscopic handle attachment 100 to be releasably secured to the endoscope proximate a handle region of the endoscope. These attachment features may vary, depending on the dimensions and other characteristics of the particular endoscope, but as an illustrative but non-limiting example, the attachment features may include hooks 124a and 124b as shown on one side of the backbone 122, and corresponding hooks 126 on the opposing side of the backbone 122 (not visible in illustrated orientation). In some cases, as will be illustrated with respect to FIG. 12, elastic members such as but not limited to O-rings may be used to secure the backbone 122 to the endoscope 100. In some cases, the attachment features may include a hook 128 and a hook 130 that are axially spaced from the hooks 124a, 124b, 126, and the hook 128 may be disposed along one side of the backbone 122 while the hook 130 may be disposed along the opposing side of the backbone 122.

The endoscope handle attachment 100 includes an upper or primary arm 140 and a lower or secondary arm 142. In this, it will be appreciated that upper and lower merely refer to the illustrated orientation. In some cases, the secondary arm 142 may be optional, for example. In some cases, the endoscope handle attachment 100 may also include additional arms. The relative size and shape of the primary arm 140 and/or the secondary arm 142 may vary, in order to accommodate particular features of the endoscope 100, or to accommodate particular features of the suture device 10 and/or any secondary devices used in combination with the suture device 10. In some cases, the primary arm 140 and/or the secondary arm 142 may be dimensioned such that devices secured to the primary arm 140 and/or the secondary arm 142 have sufficient space relative to the body of the endoscope 100. In some instances, the primary arm 140 and/or the secondary arm 142 may be straight or curved, for example. In some cases, the primary arm 140 and/or the secondary arm 142 may bifurcate in order to provide additional attachment points.

As illustrated, the primary arm 140 includes a suture device attachment member 144 and a secondary device attachment member 146. It will be appreciated that in some cases, the primary arm 140 may include the suture device attachment member 144 but may not include the secondary device attachment member 146. In some cases, the primary arm 140 may include the suture device attachment member 144, the secondary device attachment member 146 as well as one or more additional attachment members (not shown). The relative position of the suture device attachment member 144 and the secondary device attachment member 146 may be reversed, for example, or could each be located on a separate arm.

As can be seen, the suture device attachment member 144 and the secondary device attachment member 146 are both C-shaped. The suture device attachment member 144 may be configured to releasably engage the proximal handle 24 of the suture device 10 and the secondary device attachment member 146 may be configured to releasably engage the handle of a secondary device in a snap-fit arrangement, as will be shown for example in FIG. 13. In some cases, the suture device attachment member 144 and/or the secondary device attachment member 146 may be any structure that enables a quick insertion and/or release.

The secondary arm 146, which in some cases may be shorter or longer, or straight or curved, includes an external lumen attachment member 148. In some cases, the external lumen attachment member 148 includes a lumen 150. In some instances, the lumen 150 is configured to accommodate a tubular structure forming an external lumen that may be used for advancing additional instruments, fluids and the like. In some cases, the external lumen attachment member 148 may be configured such that a tubular structure including a fitting such as a luer fitting, may be advanced into the aperture 150 from a position below (in the illustrated orientation) the external lumen attachment member 148. A valve that is configured to engage the luer fitting may be lowered into the aperture 150 and engaged with the luer fitting in order to secure the external lumen to the endoscope handle attachment 100.

As noted with respect to FIG. 10, in some cases the endoscope 100 may include an instrument channel port bump out 106. In some cases, the endoscope handle attachment 120 may include an upper portion 160 that is configured to accommodate the instrument channel port bump out 106. In some instances, the upper portion 160 may include one or more tabs 162 (two are shown) that are configured to contact the instrument channel port bump out 106 and thus vertically position the endoscopic handle attachment 120 relative to the instrument channel port 108. This may be seen for example in FIG. 13.

Figure 12:
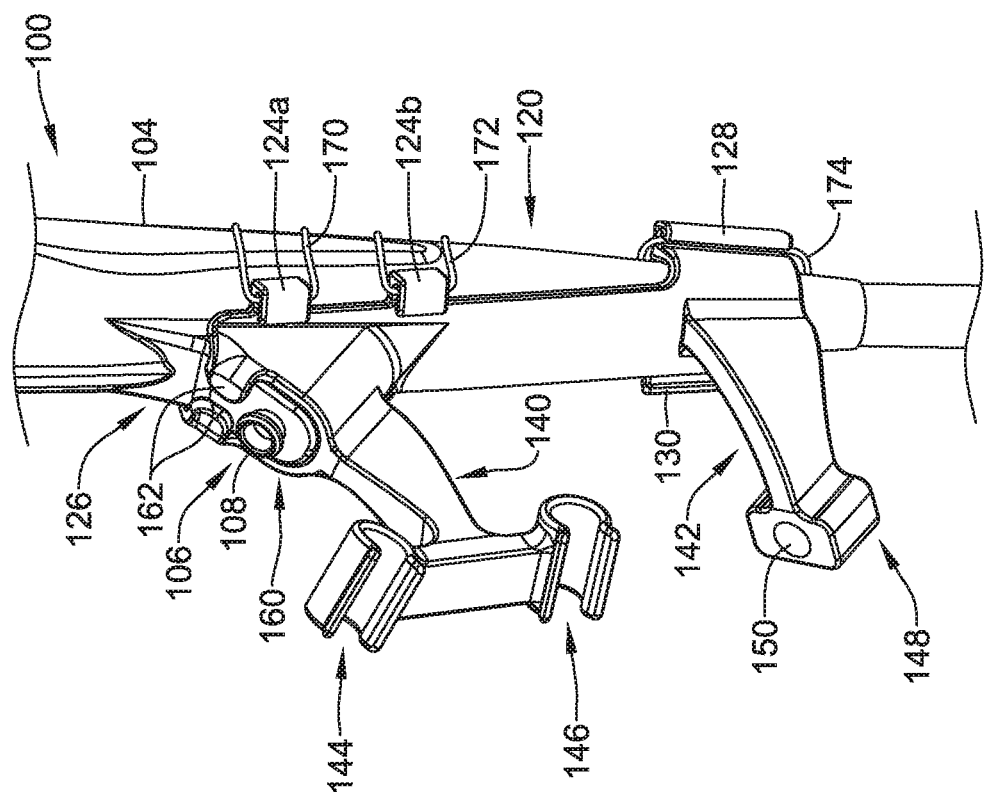
FIG. 12 is a perspective view of the endoscope attachment mechanism of FIG. 11 shown secured to the illustrative endoscope of FIG. 10 in accordance with an example of the disclosure.

In some cases, one or more elastic members may be used to secure the endoscope handle attachment 120 to the endoscope 100. As seen in FIG. 12, a first elastic member 170 may be seen as extending from the hook 124a to one of the corresponding hooks 126 (not visible). A second elastic member 172 may be seen as extending from the hook 124b to another of the corresponding hooks 126 (not shown). A third elastic member 174 extends from the hook 128 to the hook 130. As a result, the elastic members 170, 172, 174 releasably secure the endoscope handle attachment 120 to the endoscope 100. It will be appreciated that the endoscope handle attachment 120 may be removed from the endoscope 100 or repositioned relative to the endoscope 100. While elastic members 170, 172, 174 are shown, in some cases other attachment mechanisms and/or elements may be used.

Figure 13:
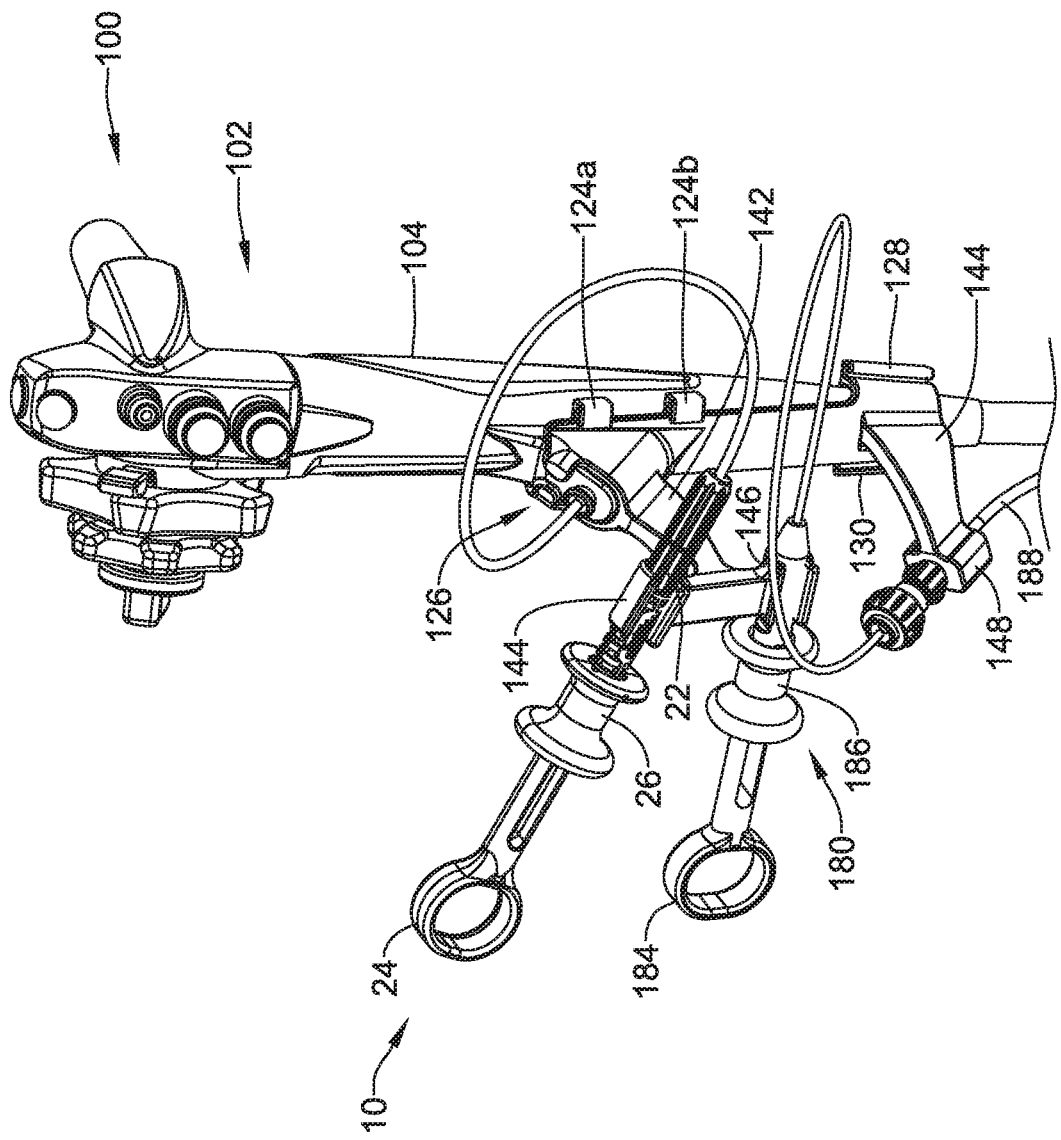
FIG. 13 is a perspective view of the illustrative endoscope of FIG. 10, including the illustrative endoscope attachment mechanism of FIG. 12 secured to the endoscope, in combination with the illustrative suture device of FIG. 1 in accordance with an example of the disclosure.

FIG. 13 shows the endoscope handle attachment 120 secured to the endoscope 100, with the suture device 10 engaged through the endoscope 100. As can be seen, the suture device 10 is secured in position via the proximal handle 24 being coupled with the suture device attachment member 144. While the endoscope handle attachment 120 is shown and described with respect to releasably securing the suture device 10, it will be appreciated that this is merely illustrative, as the endoscope handle attachment 120 may be used in combination with the endoscope 100 for releasably securing any portion of any desired medical device that may be used in combination with the endoscope 100.

The elastic members 170, 172, 174 are not shown in this view. A secondary device 180, including a proximal handle 184 and a translating handle 186 that is slidingly disposed relative to the proximal handle 184 extends through an external lumen 188 that is coupled to the external lumen attachment member 148. The secondary device 180 is secured in place by virtue of the proximal handle 184 engaging the secondary device attachment member 146. In some cases, for example, the secondary device 180 may be any device capable of being used within either the external lumen 188 or a secondary working channel of the endoscope 100. In some cases, the secondary device 180 may be a tissue graspers such as a rat tooth grasping forceps, a helical or corkscrew tissue grasper, or a fluted grasper. These are just examples.

Figure 14:
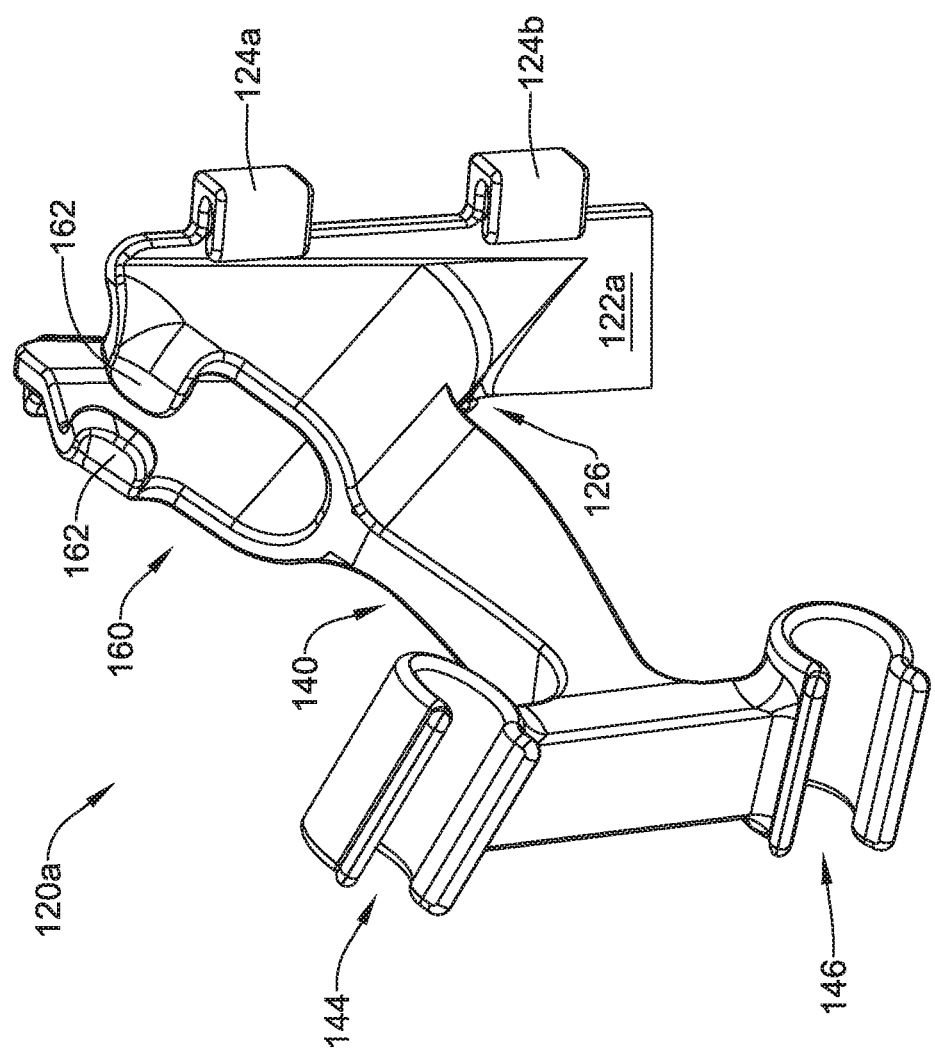
FIG. 14 is a perspective view of an illustrative endoscope attachment mechanism usable with the illustrative suture device of FIG. 1 and the illustrative endoscope of FIG. 10 in accordance with an example of the disclosure.
Figure 15:
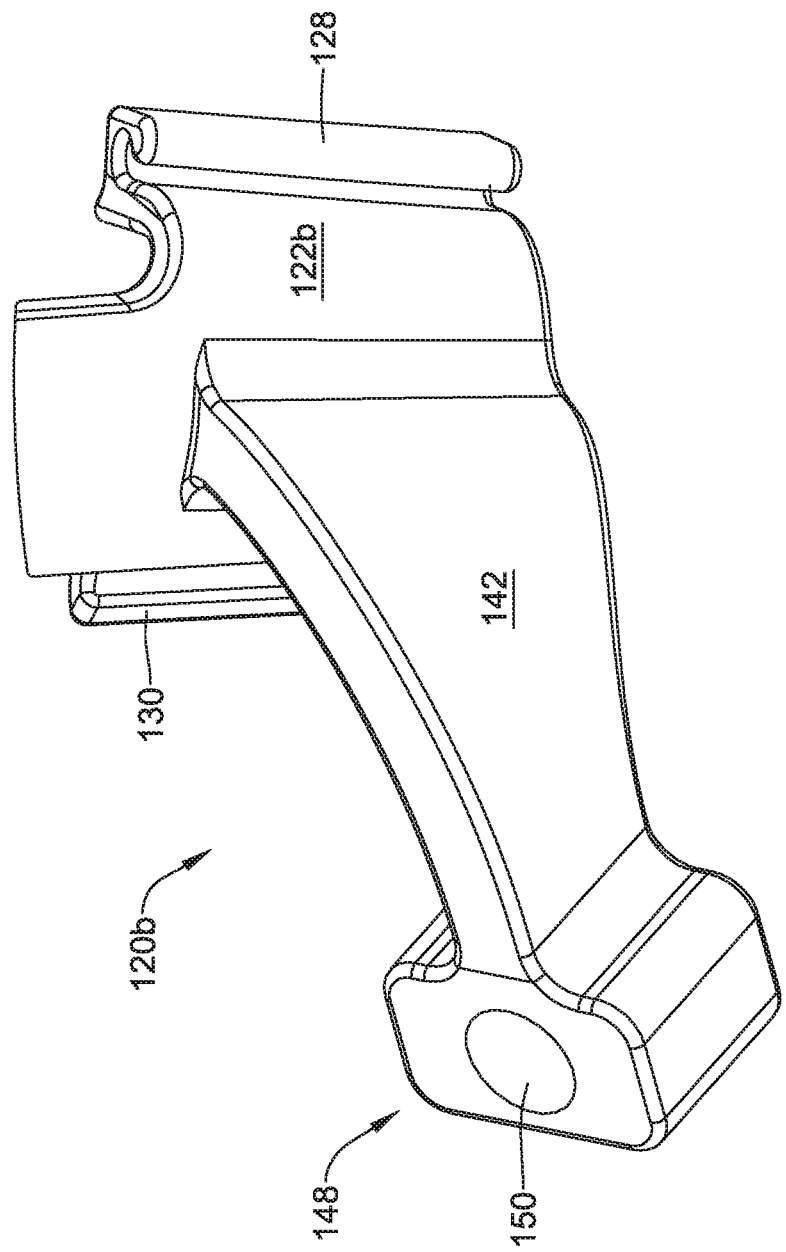
FIG. 15 is a perspective view of an illustrative endoscope attachment mechanism usable with the illustrative endoscope of FIG. 10 in accordance with an example of the disclosure.

The endoscope handle attachment 120 has been described as having a unitary backbone 122. In some cases, while not shown, the backbone 122 may include a pivoting mechanism. In some instances, as shown for example in FIGS. 14 and 15, the endoscope handle attachment 120 may be divided into an upper endoscope handle attachment 120a having a backbone portion 122a and a lower endoscope handle attachment 120b having a backbone portion 122b. In some cases, the upper endoscope handle attachment 120a may be used by itself, in combination with the lower endoscope handle attachment 120b, or in combination with the endoscope handle attachment 120. In some instances, the lower endoscope handle attachment 120b may be used by itself, in combination with the upper endoscope handle attachment 120a, or in combination with the endoscope handle attachment 120. In some cases, depending on what equipment is to be used with the endoscope 100, a pair of the upper endoscope handle attachments 120a may be used, or perhaps a pair of the lower endoscope handle attachments 120b.

It will be appreciated that a variety of different materials may be used in forming the devices described herein. In some cases, a variety of different metals may be used. Illustrative but non-limiting examples of suitable metals include titanium, stainless steel, magnesium, cobalt chromium and others. In some cases, the endoscope handle attachment 120 may be formed of materials that are resistant to the temperatures and chemicals used for disinfection. Examples include polycarbonate, ABS (acrylonitrile butadiene styrene), nylon, glass-reinforced nylon, acetal, acrylic, PET (polyethylene terephthalate), PEEK (polyetheretherketone), Pebax® and polypropylene. Additional materials that may be used can include to polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. An endoscopic handle attachment that is adapted to be secured to an endoscope having a working channel and used in combination with a suture device adapted to extend through the working channel, the suture device including a translation assembly axially translatable within the working channel and adapted to releasably engage and disengage a needle and a distal endcap securable to the distal end of the endoscope and adapted to releasable engage the needle when the translation assembly disengages the needle and to disengage the needle when the translation assembly engages the needle, the suture device including a proximal handle and a translation handle slidingly coupled to the proximal handle and operably coupled to the translation assembly such that movement of the translation handle relative to the proximal handle causes movement of the translation assembly, the endoscopic handle attachment comprising:
- a backbone adapted to conform to an outer surface of the endoscope, the backbone including one or more attachment features that are adapted to enable the endoscopic handle attachment to be releasably secured to the endoscope proximate a handle region of the endoscope;
- a primary arm extending radially outwardly from the backbone; and
- a first attachment member and a second attachment member coupled to the primary arm, at least one of the first attachment member and the second attachment member is adapted to releasably secure the proximal handle of the suture device such that the translation handle may be moved relative to the proximal handle without an operator needing to separately hold the proximal handle; wherein the first attachment member is adapted to releasably secure the proximal handle of the suture device and the second attachment member is adapted to releasably secure a handle for a secondary device used in combination with the suture device.

2. The endoscopic handle attachment of claim 1, wherein the one or more attachment features comprise hook structures that are formed into the backbone and are adapted to secure one or more elastic members that engage the hook structures and extend around the endoscope.

3. The endoscopic handle attachment of claim 2, wherein the hook structures comprise a first hook on a first side of the backbone and an opposing second hook on a second side of the backbone.

4. The endoscopic handle attachment of claim 1, wherein the first attachment member comprises a C-shaped attachment member into which the proximal handle of the suture device is releasably engageable via a snap fit.

5. The endoscopic handle attachment of claim 1, further comprising a secondary arm having an attachment member adapted to releasably secure an external lumen used with the suture device.

6. The endoscopic handle attachment of claim 5, wherein the attachment member of the secondary arm includes an aperture extending through the attachment member such that a fitting of the external lumen may be extended upwardly through the aperture and a valve may be extended down into the aperture to engage the fitting and thus releasably secure the external lumen to the attachment member of the secondary arm.

7. The endoscopic handle attachment of claim 5, wherein the secondary device is adapted to extend from the handle releasably secured to the second attachment member of the primary arm and into the external lumen releasably secured to the attachment member of the secondary arm.

8. The endoscopic handle attachment of claim 6, wherein the upper portion adapted to fit about the instrument channel port bump out includes one or more tabs adapted to contact the instrument channel port bump out and thus vertically position the endoscopic handle attachment relative to the instrument channel port.

9. The endoscopic handle attachment of claim 1, wherein the endoscope includes an instrument channel port that is fluidly coupled with the working channel, and the backbone includes an upper portion adapted to fit about an instrument channel port bump out accommodating the instrument channel port.

10. An endoscopic handle attachment that is adapted to be secured to an endoscope having a working channel and used in combination with a suture device adapted to extend through the working channel, the suture device including a translation assembly axially translatable within the working channel and a distal assembly and adapted to pass a needle back and forth between the translation assembly and the distal assembly, the suture device including a proximal handle and a translation handle slidingly coupled to the proximal handle and operably coupled to the translation assembly, the endoscopic handle attachment comprising:
- a backbone adapted to conform to an outer surface of the endoscope, the backbone including one or more attachment features that are adapted to enable the endoscopic handle attachment to be releasably secured to the endoscope proximate a handle region of the endoscope;
- a primary arm extending radially outwardly from the backbone;
- a suture device attachment member coupled to the primary arm and adapted to releasably secure the proximal handle of the suture device such that the translation handle may be moved relative to the proximal handle without an operator needing to separately hold the proximal handle; and
- a secondary device attachment member coupled to the primary arm and adapted to releasably engage a handle of a secondary device adapted to be used in combination with the suture device.

11. The endoscopic handle attachment of claim 10, further comprising a secondary arm extending radially outwardly from the backbone and including an external lumen attachment member, the external lumen attachment member including an aperture extending through the external lumen attachment member such that a fitting of the external lumen may be extended upwardly through the aperture and a valve may be extended down into the aperture to engage the fitting and thus releasably secure the external lumen to the external lumen attachment member.

12. The endoscopic handle attachment of claim 10, wherein the one or more attachment features comprise hook structures that are formed into the backbone and are adapted to secure one or more elastic members that engage the hook structures and extend around the endoscope.

13. The endoscopic handle attachment of claim 12, wherein the hook structures comprise a first hook on a first side of the backbone and an opposing second hook on a second side of the backbone.

14. The endoscopic handle attachment of claim 10, wherein the suture device attachment member is adapted to releasably engage the proximal handle of the suture device via a snap fit.

15. The endoscopic handle attachment of claim 10, wherein the secondary device attachment member is adapted to releasably engage the handle of the secondary device via a snap fit.

16. The endoscopic handle attachment of claim 10, wherein the endoscope includes an instrument channel port that is fluidly coupled with the working channel, and the backbone includes an upper portion adapted to fit about an instrument channel port bump out accommodating the instrument channel port, the upper portion including one or more tabs adapted to contact the instrument channel port bump out and thus vertically position the endoscopic handle attachment relative to the instrument channel port.

17. A suture assembly for use in combination with an endoscope having a working channel and a distal end, the suture assembly comprising:
- a translation assembly axially translatable within the working channel and including:
  - a needle configured to carry a suture;

a distal shuttle configured to releasably secure the needle; and a sleeve disposable over the distal shuttle, the sleeve movable between a locked position in which the needle is secured to the distal shuttle and an unlocked position in which the needle is releasable from the distal shuttle;

a distal endcap securable to the distal end of the endoscope and configured to engage the needle when the needle is advanced distally into the endcap and to release the needle when the needle is locked to the distal shuttle and the distal shuttle is withdrawn proximally;

a proximal handle;

a translating handle slidingly disposed relative to the proximal handle and operably coupled to the translation assembly;

a backbone adapted to conform to an outer surface of the endoscope and to be releasably secured to the endoscope proximate an instrument channel port of the endoscope;

an arm extending radially outwardly from the backbone;

a suture assembly attachment member coupled to the arm and adapted to releasably secure the proximal handle such that the translation handle may be moved relative to the proximal handle without an operator needing to separately hold the proximal handle; and a secondary device attachment member coupled to the arm for securing a handle of a secondary device used in combination with the suture assembly.

18. The suture assembly of claim 17, further comprising a second arm bearing an external lumen attachment member.

* * * * *